(12) United States Patent
Sharma et al.

(10) Patent No.: US 12,114,837 B2
(45) Date of Patent: Oct. 15, 2024

(54) ENDOSCOPE ACCESSORY CONTROLS AND METHODS OF USE

(71) Applicants: Boston Scientific Scimed, Inc., Maple Grove, MN (US); Boston Scientific Medical Device Limited, Galway (IE)

(72) Inventors: Deepak Kumar Sharma, Muzaffarnagar (IN); Barry Weitzner, Acton, MA (US)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 52 days.

(21) Appl. No.: 17/806,780

(22) Filed: Jun. 14, 2022

(65) Prior Publication Data
US 2023/0000310 A1    Jan. 5, 2023

Related U.S. Application Data

(60) Provisional application No. 63/216,994, filed on Jun. 30, 2021.

(51) Int. Cl.
*A61B 1/00* (2006.01)
*A61B 1/005* (2006.01)
*A61B 1/018* (2006.01)

(52) U.S. Cl.
CPC ........ *A61B 1/0052* (2013.01); *A61B 1/00042* (2022.02); *A61B 1/00087* (2013.01); *A61B 1/0057* (2013.01); *A61B 1/018* (2013.01)

(58) Field of Classification Search
CPC .............. A61B 1/0052; A61B 1/00042; A61B 1/00087; A61B 1/0057; A61B 1/018;
(Continued)

(56) References Cited

U.S. PATENT DOCUMENTS

| 4,852,550 A | 8/1989 | Koller et al. |
| 5,993,466 A | 11/1999 | Yoon |

(Continued)

FOREIGN PATENT DOCUMENTS

| EP | 2962644 A1 | 1/2016 |
| JP | 4801213 B2 | 10/2011 |

(Continued)

OTHER PUBLICATIONS

International Search Report and Written Opinion issued in International Application No. PCT/US2022/072920, issued Oct. 6, 2022 (12 pages).

*Primary Examiner* — Timothy J Neal
*Assistant Examiner* — James Edward Boice
(74) *Attorney, Agent, or Firm* — Bookoff McAndrews, PLLC (57) ABSTRACT

A medical device includes a handle including a first slot, a first control device movable within the first slot in a proximal direction and a distal direction, and a sheath extending from the handle and having a longitudinal axis, the sheath defining a first lumen extending from the handle to a distal end of the sheath. A first tube extends within the first lumen, the first tube is connected to the first control device and moves between a first position, where a distalmost end of the first tube is flush with or proximal of a distalmost end of the sheath, and a second position, where the distalmost end of the first tube is positioned distal of the distalmost end of the sheath. The first slot extends parallel to the longitudinal direction of the sheath.

13 Claims, 9 Drawing Sheets

(58) Field of Classification Search
CPC ............ A61B 1/00066; A61B 17/2909; A61B 2017/291; A61B 2017/2923; A61B 2017/2946; A61B 2017/2948; A61B 2017/00973; A61B 2017/2927
USPC ........................................................ 600/106
See application file for complete search history.

(56) References Cited

U.S. PATENT DOCUMENTS

| | | |
|---|---|---|
| 8,083,669 B2 | 12/2011 | Murakami et al. |
| 9,456,736 B2 | 10/2016 | Onuki et al. |
| 10,299,874 B2 | 5/2019 | Weitzner et al. |
| 2004/0193016 A1 | 9/2004 | Root et al. |
| 2011/0004058 A1 | 1/2011 | Oneda et al. |
| 2011/0046439 A1* | 2/2011 | Pamnani .......... A61B 17/00008 600/104 |
| 2011/0163146 A1 | 7/2011 | Ortiz et al. |
| 2013/0267950 A1 | 10/2013 | Rosa et al. |
| 2017/0010457 A1* | 1/2017 | Nishijima ............ A61B 1/0051 |
| 2018/0263688 A1 | 9/2018 | Barrish et al. |
| 2018/0333044 A1 | 11/2018 | Jenkins |
| 2019/0208994 A1* | 7/2019 | Davis ................. A61B 1/00133 |
| 2019/0231466 A1 | 8/2019 | Weitzner et al. |

FOREIGN PATENT DOCUMENTS

| | | |
|---|---|---|
| JP | 2019088716 A | 6/2019 |
| WO | 2007086073 A2 | 8/2007 |
| WO | 2008095046 A2 | 8/2008 |
| WO | 2012138834 A2 | 10/2012 |

* cited by examiner

ENDOSCOPE ACCESSORY CONTROLS AND METHODS OF USE

CROSS-REFERENCE TO RELATED APPLICATIONS

This application claims the benefit of priority of U.S. Provisional Patent Application No. 63/216,994, filed Jun. 30, 2021, the entirety of which is incorporated herein by reference.

TECHNICAL FIELD

The present disclosure relates generally to endoscopic medical devices and related methods of use. More particularly, in some embodiments, the disclosure relates to using one or more accessory devices or medical instruments with an endoscope and independent articulation of a distal end of each of the endoscope and the one or more accessory devices or medical instruments.

BACKGROUND

Medical tools for accessing target sites within a body may be advanced through one or more lumens of an endoscope, and may extend from a distal end thereof to manipulate the target site. Drawbacks of these endoscopic systems include, for example, limited accessibility and maneuverability of tools at protruding from the distal end of the endoscope. For example, in many endoscopes, medical tools extend from one or more openings in a distal end face of the endoscope, limiting the access and maneuverability of these medical tools in a direction perpendicular to the distal end face. This may create difficulties in cutting and removing tissue from the target sites, or performing other therapies. Furthermore, multiple users, such as a physician and one or more technicians, may be required to operate multiple tools and/or accessories of an endoscope device. This may increase the number of persons in a medical operation suite, which may increase the risk of accidents, infections, or other complications. The present disclosure may solve one or more of these problems or other problems in the art. The scope of the disclosure, however, is defined by the attached claims and not the ability to solve a specific problem.

SUMMARY OF THE DISCLOSURE

According to an aspect, a medical device includes a handle including a first slot, a first control device configured to move within the first slot in a proximal direction and a distal direction, and a sheath extending from the handle and having a longitudinal axis, the sheath defining a first lumen extending from the handle to a distal end of the sheath, a first tube extending within the first lumen, wherein the first tube is connected to the first control device and is configured to move between a first position, where a distalmost end of the first tube is flush with or proximal of a distalmost end of the sheath, and a second position, where the distalmost end of the first tube is positioned distal of the distalmost end of the sheath, wherein the first slot extends parallel to the longitudinal direction of the sheath.

The first tube may be configured to move between the first position and the second position as the first control device moves from a proximal end of the first slot in the distal direction.

The first control device may include a locking mechanism configured to prevent movement of the first control device and maintain a position of the first control device relative to the handle in the proximal direction and in the distal direction.

The locking mechanism may include an annular ring extending radially outward from the first tube, wherein the annular ring may contact a portion of the handle and increases a friction force between the handle and the first tube, and wherein the first control device may be configured to move within the first slot when a force sufficient to overcome the friction force of the annular ring is applied to the first control device.

The first control device may include a joystick, and wherein movement of the joystick may be configured to bend a distal end of the first tube at an angle relative to the longitudinal axis of the sheath.

The device may further include at least three articulation wires extending from the joystick to the distal end of the first tube, wherein a distal end of each of the at least three articulation wires may be attached to the first tube.

The first tube may include an articulation wire lumen corresponding to each of the at least three articulation wires, and wherein each of the at least three articulation wires may extend within the corresponding articulation wire lumens.

The first tube may include a tube lumen, and wherein the device may further include a medical instrument configured to be inserted into the tube lumen, and wherein a distalmost end of the medical instrument may be configured to extend distally of the distalmost end of the sheath.

The device may further include a rotatable locking mechanism at a proximal end of the tube lumen, wherein the rotatable locking mechanism may be configured to fluidly seal the medical instrument in the tube lumen when the rotatable locking mechanism is in a locked position, and wherein the medical instrument may be configured to move within the tube lumen when the rotatable locking mechanism is in an unlocked position.

The medical instrument may include a tool at its distal end, and wherein the device may further include an actuator configured to actuate the medical instrument.

The tool may include a plurality of jaws connected by a hinge, wherein the actuator may include a foot pedal, wherein the plurality of jaws may be configured to move from an open position to a closed position when the foot pedal is depressed, and wherein the plurality of jaws may be configured to move from the closed position to the open position when the foot pedal is released.

The device may further include a second lumen within the sheath and extending from the handle to the distal end of the sheath, and a second tube extending within the second lumen, wherein the second tube may be configured to move between a first position, where a distalmost end of the second tube may be flush with or proximal of the distalmost end of the sheath, and a second position, where the distalmost end of the second tube is positioned distal of the distalmost end of the sheath.

The device may further include a second slot, and a second control device configured to move within the second slot, wherein the second control device may include a second joystick configured to cause a distal end of the second tube to bend.

The first control device and the second control device may be configured to move independently of each other, and wherein the first tube and the second tube may be configured to bend independently of each other.

The handle may include a first handle actuator and a second handle actuator configured to deflect a portion of the sheath.

According to another aspect, a medical device includes a handle, a first control device and a second control device, a sheath extending from the handle and having a longitudinal axis, the sheath defining a first lumen and a second lumen, a first tube extending from the first control device and within the first lumen, and a second tube extending from the second control device and within the second lumen. The first control device is configured to bend a portion of the first tube, wherein the second control device is configured to bend a portion of the second tube, and wherein the first tube and the second tube are configured to be bent independently from each other.

The device may further include a first locking mechanism on the first control device and a second locking mechanism on the second control device, wherein the first locking mechanism and the second locking mechanism may be configured to prevent movement of the first control device and the second control device relative to the handle.

The first control device and the second control device may be configured to move longitudinally relative to the handle, and wherein the first control device may be configured to move independently of the second control device.

According to yet another aspect, a method may include inserting a shaft of an insertion device into a body via an opening, advancing the insertion device so that a distal end of the insertion device is adjacent to a target site, deploying a first tube from the shaft of the insertion device via an opening an a distal end of a first lumen, advancing a first medical instrument through a lumen of the first tube, and out of an opening at a distal end of the first tube, and bending a portion of the first tube extending from the shaft at an angle relative to a longitudinal axis of the shaft.

The method may further include deploying a second tube from the shaft of the insertion device via an opening in a second lumen of the shaft, advancing a second medical instrument through a lumen of the first tube, and out of an opening at a distal end of second first tube, and bending a portion of the second tube extending from the shaft at an angle relative to the longitudinal axis of the shaft, wherein bending the first tube may include actuating a first joystick attached to a handle extending from a proximal end of the shaft, wherein bending the second tube may include actuating a second joystick attached to the handle, and wherein the first tube and the second tube may be configured to bend independently of each other.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

The present disclosure is described with reference to exemplary medical systems and medical tools for accessing a target site, for example, for accessing a target site from different directions and/or different angles at a distal end of an endoscope. This may provide improved medical tool functionality and/or assist medical professionals to gain improved access to the target site for performing medical procedures. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface refer to exact and approximate shapes.

Figure 1:
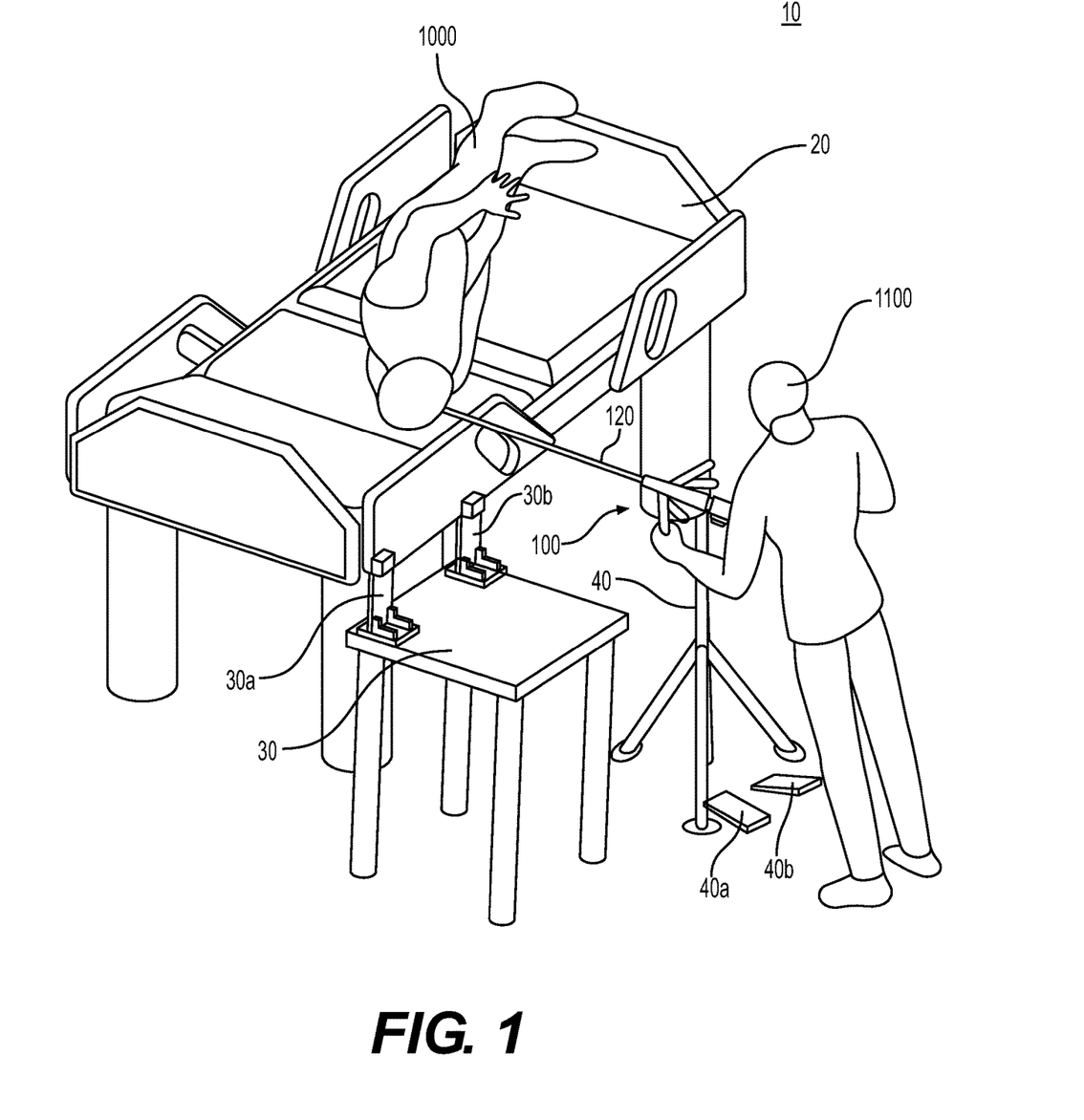
FIG. 1 is a schematic view of a medical system according to an embodiment.

Referring to FIG. 1, a medical system 10 according to an embodiment is shown. Medical system 10 may include a patient table 20 for supporting a patient 1000 (or a portion of patient 1000, e.g., a leg, an arm, etc.), a table 30 (or other support device) for supporting one or more actuating devices 30a, 30b, and a support device 40, which may support an endoscope system 100 (e.g., an insertion device). Actuating devices 30a, 30b may receive one or more medical devices that may be delivered to a target site in patient 1000, for example, via endoscope system 100, as described herein. A user 1100 may operate endoscope system 100, including actuators 40a, 40b (e.g., foot pedals, which may be wireless or wired (wires not shown)), to cause actuation of actuating devices 30a, 30b and cause actuation of one or more portions of endoscope system 100, as described herein.

Figure 2:
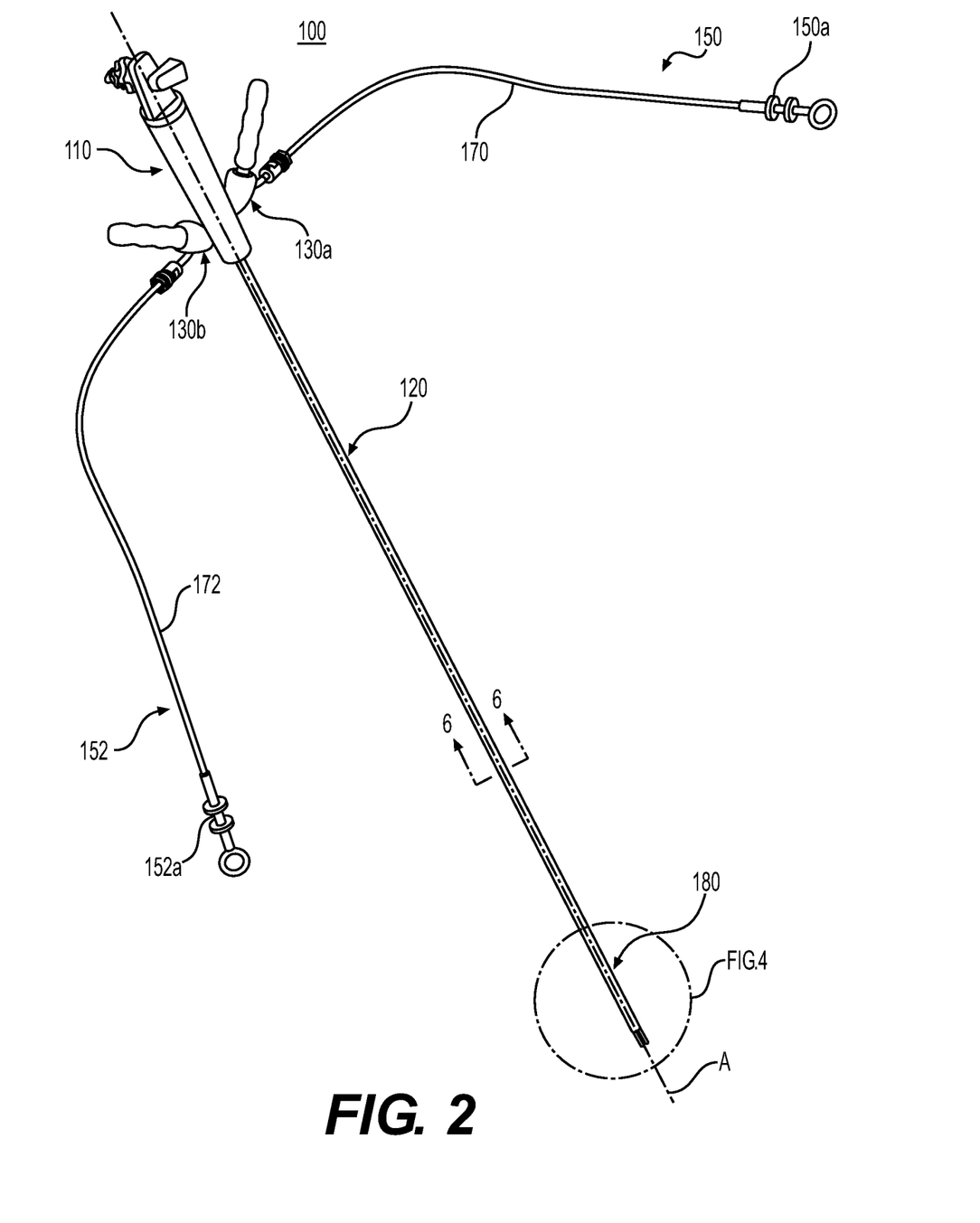
FIG. 2 is a schematic view of an endoscope system of FIG. 1, according to an embodiment.

As shown in FIG. 2, endoscope system 100 includes a handle 110. Handle 110 may be supported by support device 40 in FIG. 1 via a clip, a strap (not shown), a screw attaching to a threaded member in handle 110 (not shown), or any other attachment mechanism. While support device 40 is shown as a three-legged support member (e.g., a tri-pod), support device 40 may be a four-legged support member (such as a table) or any other support device having any number of legs. Support device 40 may support handle 110 in a fixed manner relative to patient 1000 and/or table 20 to enable user 1100 to perform one or more medical procedures on patient 1000, as described herein.

With continued reference to FIG. 1, actuating devices 30*a*, 30*b* may be supported on table 30. While two actuating devices 30*a*, 30*b* are shown, any number of actuators may be provided. Actuating device 30*a* may receive a handle 150*a* of a first medical instrument 150 shown in FIG. 2, and actuating device 30*b* may receive a handle 150*b* of a second medical instrument 152 shown in FIG. 2. As described herein, actuating devices 30*a*, 30*b* may be actuated to cause actuation of first medical instrument 150 and/or second medical instrument 152 (e.g., one or more tools or end effectors at a distal end of first medical instrument 150 and/or second medical instrument 152). It will be understood that while actuating devices 30*a*, 30*b* are supported by table 30, actuating devices 30*a*, 30*b* may be attached to and may be supported by any other device of medical system 10, including support device 40, patient table 20, or the like.

With reference to FIG. 2, endoscope system 100 may include handle 110, a shaft 120 (e.g., a catheter) connected to a distal end of handle 110, and a distal end effector 180 at a distal end of shaft 120. Shaft 120 may be flexible and may be formed of any medical grade material suitable for accessing a tortuous path within the body, but the rigidity/flexibility of shaft 120 is not limited. Endoscope system 100 may be an endoscope, a colonoscope, a bronchoscope, an ureteroscope, a duodenoscope, or other like-device (not shown).

Figure 3:
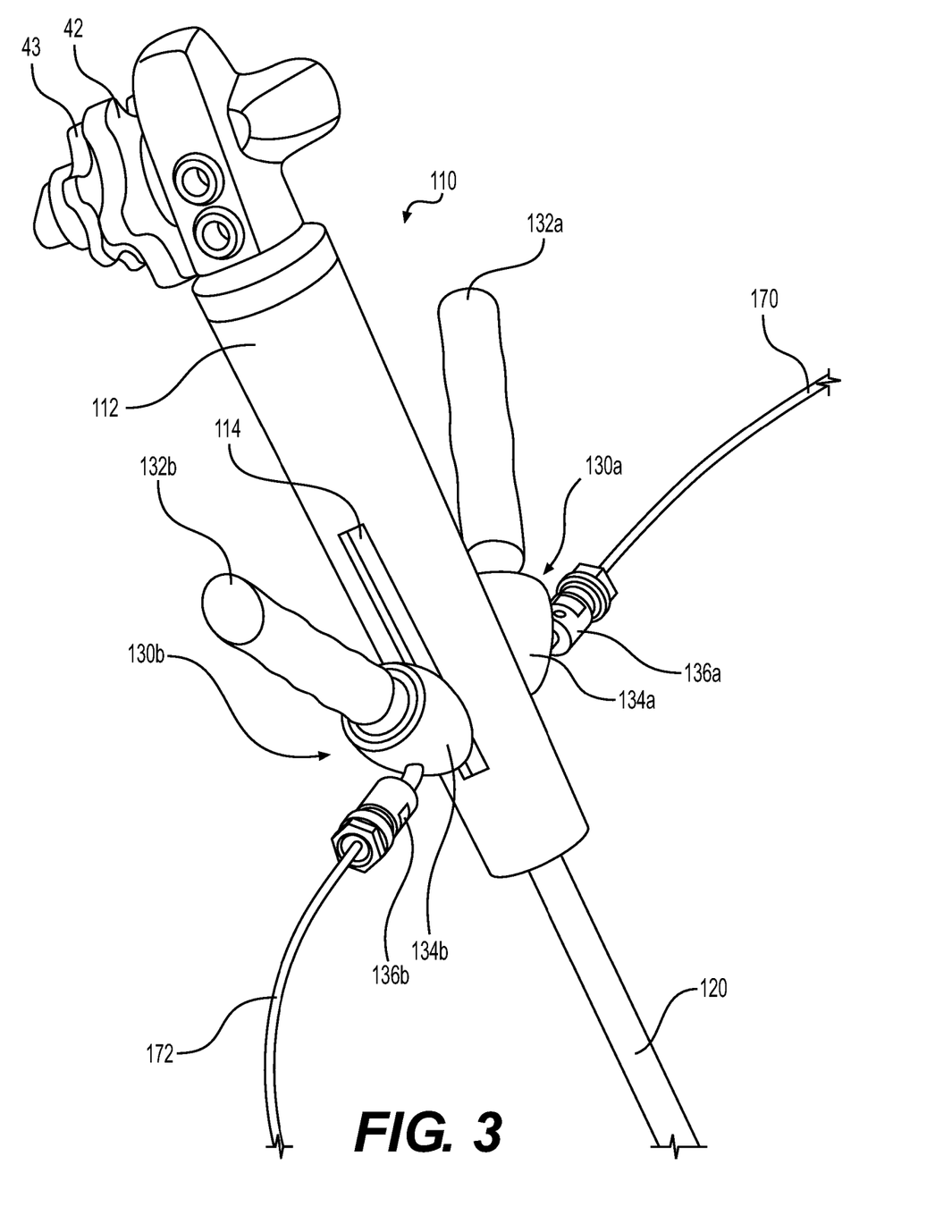
FIG. 3 is a proximal end of the endoscope system of FIG. 2, according to an embodiment.
Figure 6:
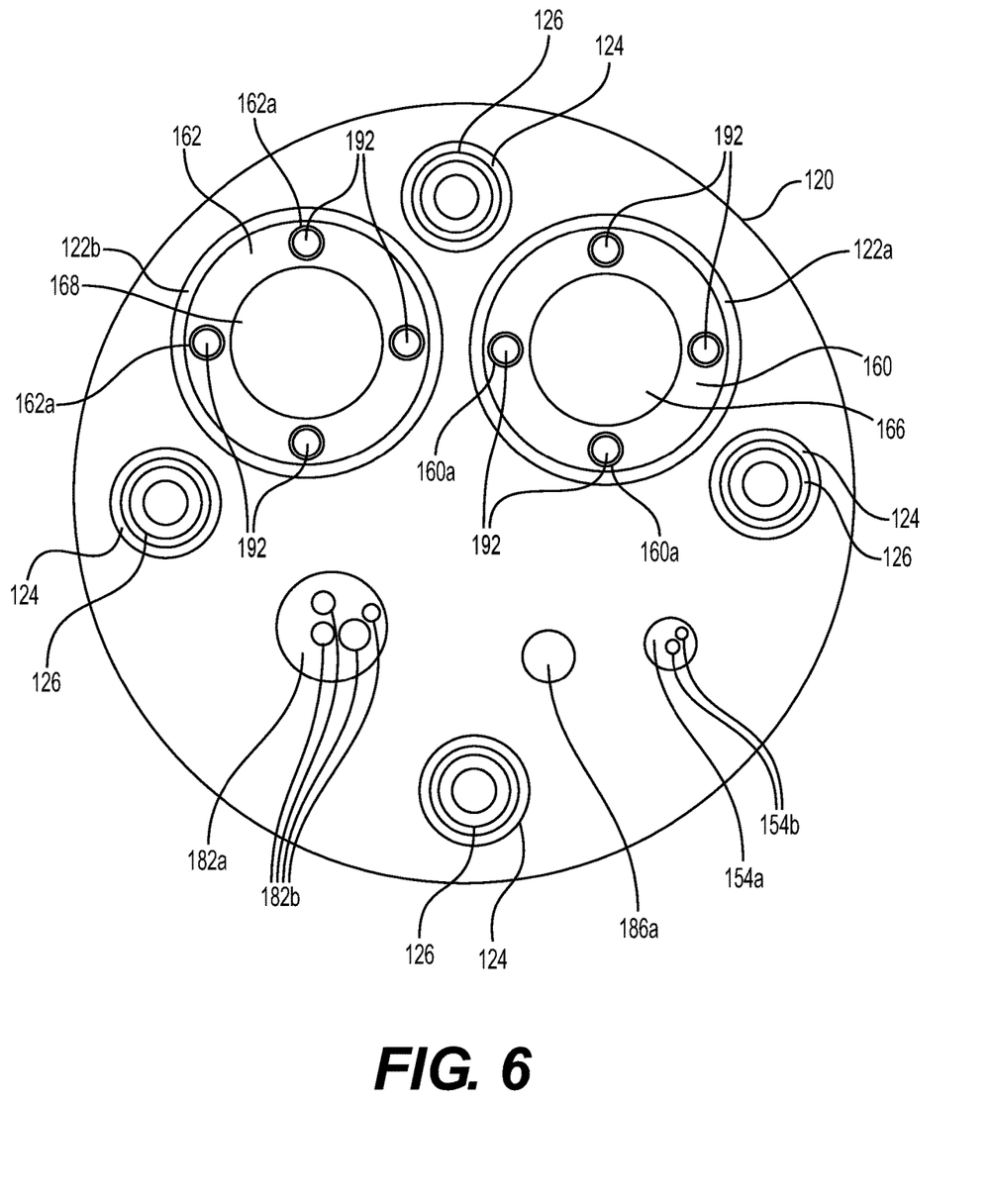
FIG. 6 is a cross-section along the line 6-6 in FIG. 2, according to an embodiment.

As shown in FIG. 3, handle 110, or a similar device for actuating or controlling endoscope system 100 and any tools, devices, or instruments associated with endoscope system 100, includes first and second actuating devices 42, 43. Devices 42, 43 control articulation of shaft 20, and/or an articulation joint at or proximal to distal end 180 of shaft 120, in multiple directions. Devices 42, 43 may be, for example, rotatable knobs that rotate about their axes to push/pull actuating elements 126 which extend within actuating lumen 124 of shaft 120 (FIG. 6). Actuating elements 126, such as cables or wires suitable for medical procedures (e.g., medical grade plastic or metal), extend distally from a proximal end of endoscope system 100 and connect to shaft 120 to control movement thereof. Alternatively, or additionally, a user may operate actuating elements 126 independently of handle 110. Distal ends of actuating elements 126 extend through actuating lumens 124 of shaft 120 and terminate at an actuating joint and/or distal end 180 of shaft 120. It will be understood that the actuating joint may be part of distal end 180, or the actuating joint may be attached to a distal end of shaft 120 and a proximal end of distal end 180. For example, one or more actuating elements 126 may be connected to an articulation joint, and actuation of actuating elements 126 may control the actuating joint or distal end 180 of shaft 120 to move in multiple directions.

One or more electrical cables (such as electrical cables 154*b* disposed in an imaging lumen 154*a* or electrical cables 182*b* disposed in a light lumen 182*a*, shown in FIG. 6) may extend from the proximal end of shaft 120 to distal end 180 of shaft 120. Cables (e.g., cables 154*b* or 182*b*) may provide electrical controls to imaging, lighting, and/or other electrical devices at distal end 180 of shaft 120, and may carry imaging signals proximally from or distally to an imaging device 182 (e.g., a camera or other image sensor) and/or a light emitting device 184 at distal end 180 of shaft 120 (FIG. 5F), for example, to send signals from a user interface to imaging device 182 and/or light emitting device 184, to carry signals from imaging device 182 to be processed and/or displayed on a display, etc.

Handle 110 may also include one or more ports, such as ports 136*a*, 136*b* shown in FIG. 3 and described below, or a port 200 connected to a suction/irrigation lumen 186*a* shown in FIG. 6. In these aspects, ports 136*a*, 136*b*, and 200 may be used for introducing and/or removing tools, fluids, or other materials from the patient. As described herein, ports 136*a*, 136*b* may be used to introduce tools or instruments, e.g., first and second medical instruments 150, 152, respectively. Port 200 connected to suction/irrigation lumen 186*a* may be connected to an umbilicus for introducing fluid and/or suction. Further, the umbilicus may include the wiring for electronic components (e.g., wiring connected to cables 154*b* and/or 182*b*). An opening 186 at a distal end of suction lumen 186*a* is shown in FIG. 5F.

Figure 5A:
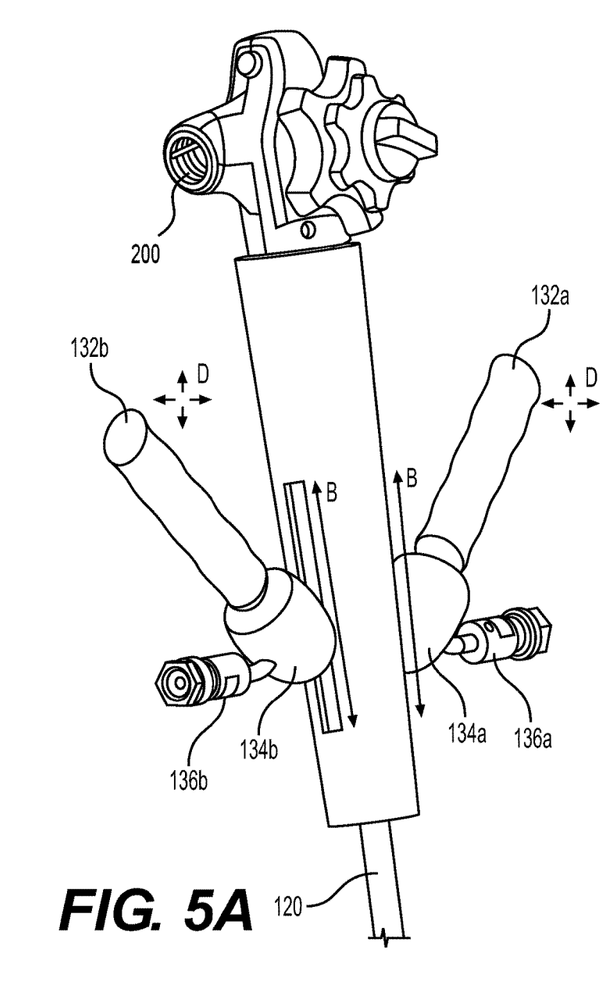
FIG. 5A is a proximal end of the endoscope system of FIG. 2, according to an embodiment.
Figure 5B:
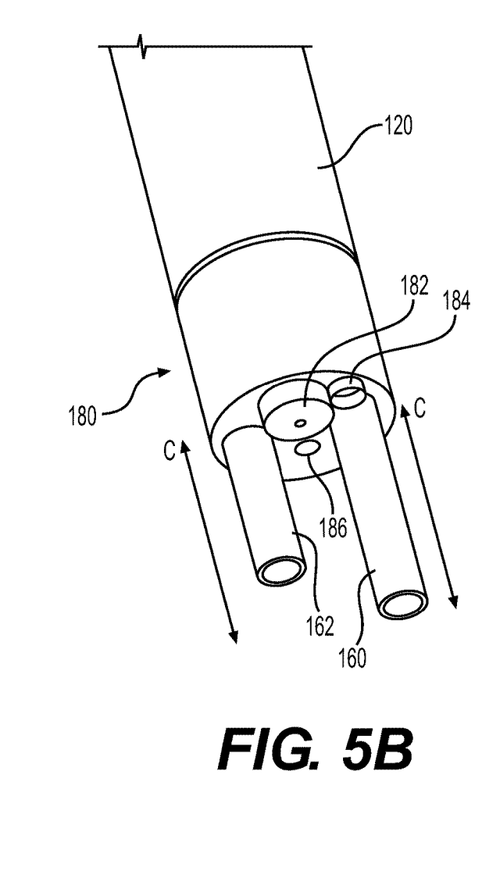
FIGS. 5B and 5C are views of a distal end of the endoscope system of FIG. 2, according to an embodiment.

With reference to FIG. 2, control devices 130*a*, 130*b* are connected to handle 110 and may move in a proximal-distal direction relative to handle 110, as shown by arrow B (FIG. 5A). Control devices 130*a*, 130*b* are disposed on outer surfaces of handle 110 and may be oriented approximately 180 degrees from each other around a circumference of handle 110. It will be understood, however, that handle 110 may include only one control device 130*a*, or may include three, four, or more control devices 130*a*, 130*b*, . . . 130*n*, and control devices 130*a*, 130*b* may be disposed at any position about the circumference of handle 110. For ease of understanding, reference will be made to control device 130*a*, but the description of control device 130*a* will apply equally to control device 130*b* (and any additional control devices on handle 110) unless stated otherwise.

Figure 8:
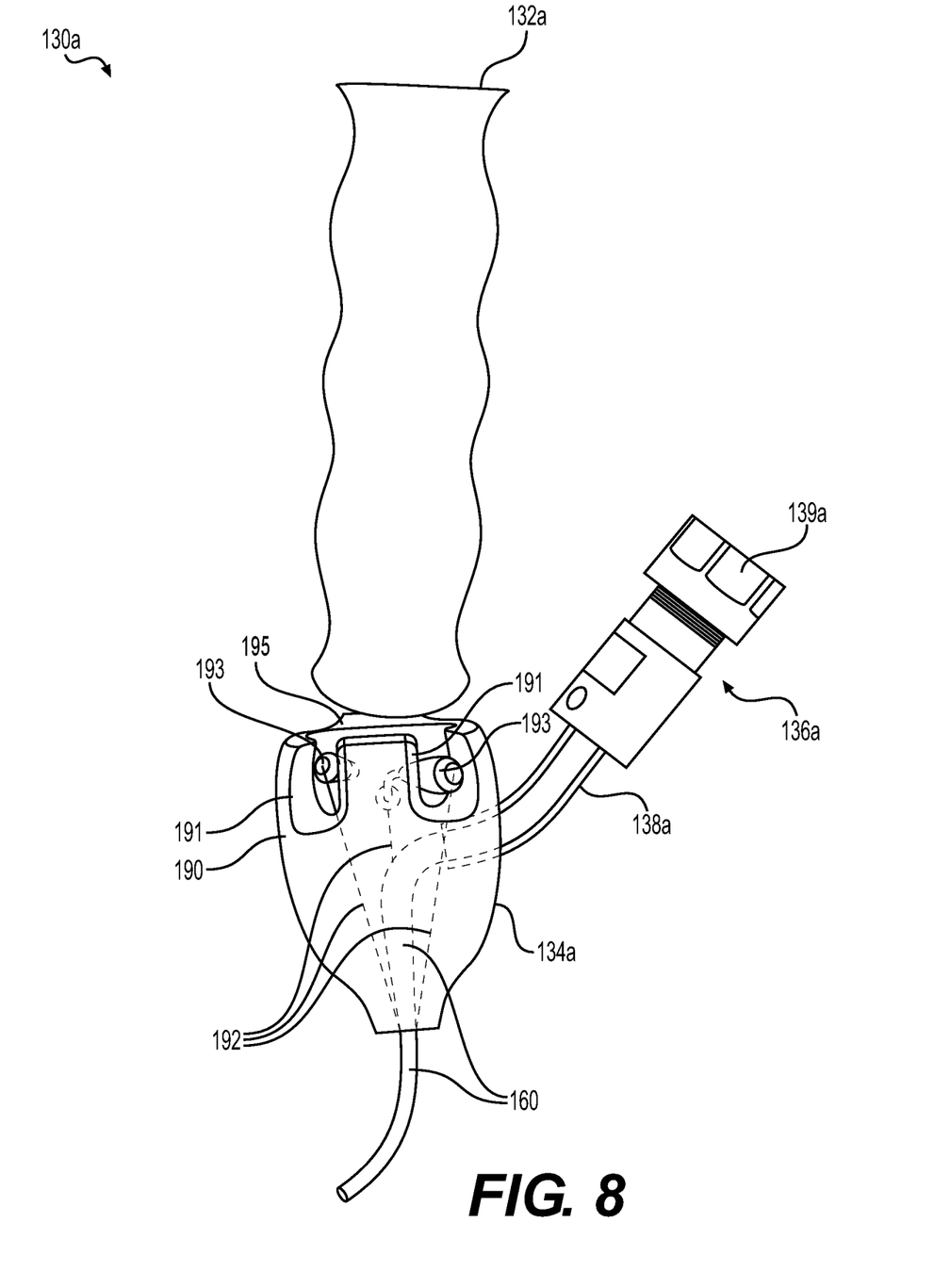
FIG. 8 illustrates a control device of the endoscope system of FIG. 2, according to an embodiment.

With reference to FIGS. 2 and 8, control device 130*a* includes a joystick 132*a* having a ball bearing 195 attached to one end. Ball bearing 195 may be generally spherical and may be disposed within a generally spherical opening within a socket 191 of a housing 190. Ball bearing 195 is configured to move in any direction, for example, 360-degrees, within socket 191 when a user (e.g., physician 1100 in FIG. 1) applies a force to joystick 132*a* in any direction, as shown by arrows D in FIG. 5A. Ball bearing 195 may sit within housing 190 of socket 191 and may be supported by and/or may contact one or more inner walls of housing 190. The inner walls of housing 190 may define a movement direction of ball bearing 195.

Ball bearing 195 may have a plurality of protrusions 193 extending radially outward from ball bearing 195. Protrusions 193 may be any elements (e.g., slits, holes, openings, etc.) in ball bearing 195 for coupling one or more actuation wires 192 to ball bearing 195). Protrusions 193 may move within slots (unlabeled) in socket 191 to allow ball bearing 195 to move in any direction, described herein. Attached to each protrusion 193 is an actuation wire 192. While three actuation wires 192 are shown in FIG. 8, it will be understood that any number of actuation wires 192 may be used (e.g., two, four, five, etc.), based on the number of protrusions 193 extending from ball bearing 195. Each actuation wire 192 extends from its respective protrusion 191 in a distal direction and connects to a distal end of a first tube 160 (first tube 160 shown in FIG. 4) (e.g., a working channel). In this manner, as discussed below, movement of ball bearing 195 within socket 191 may push or pull one or more of actuation wires 192, and thus manipulate the distal end of first tube 160. It will be understood that additional wires 192 may provide improved maneuverability of control device the distal end of first tube 160, as described herein. First tube 160 may have a diameter of approximately 2.8 mm, but may be any size and is not limited thereto. It will be understood that first tube 160 may be sized to fit within first lumen 122*a*, the size of which is also not limited. In some examples, a diameter of first tube 160 may be approximately 1.0 mm to approximately 10.0 mm, and a diameter of first lumen 122a may be approximately 0.010 inches greater than the diameter of first tube 160.

With continued reference to FIG. 8, a proximal end of first tube 160 extends through an opening in a distal end of control device 130a, through a lumen (unlabeled) of control device 130a, and through an opening in a side surface of control device 130a. A proximal end of first tube 160 (identified as 138a in FIG. 8) terminates in port 136a, which may include a collet. The collet of port 136a may include a locking member 139a. Locking member 139a may include an opening covered by a movable membrane (not shown) that may provide a seal (i.e., form a fluid seal) between locking member 139a and a shaft 170 of first medical instrument 150 (FIG. 2). For example, locking member 139a may be a screw-type device and may rotate about an axis via screw threads. When shaft 170 of first medical instrument 150 is inserted into the opening of locking member 139a, locking member 139a may be rotated in a first direction to lock shaft 170 relative to locking member 139a and create a seal between shaft 170 and locking member 139a. Locking member 139a may be rotated in a second direction, opposite the first direction, to unlock shaft 170 relative to locking member 139a.

With reference to FIGS. 3 and 5A, a slot 114 may extend in a proximal-distal direction relative to a longitudinal axis A of endoscope system 100 (see FIG. 2 for longitudinal axis A). Slot 114 may be provided on both sides of handle 110 and may be configured to allow control devices 130a, 130b to move in respective slots 114 in proximal and distal directions. For example, control device 130a may be moved in proximal and distal directions within a slot (not shown) as indicated by arrow B in FIG. 5A. Control device 130b may also move in a slot 114 in proximal and distal directions indicated by arrow B. Movement of control device 130a may allow a distal end of first tube 160 to move proximally and distally in the direction indicated by arrow C shown in FIG. 5B. For example, distal movement of control device 130a may cause a distalmost end of first tube 160 to extend distally of a distalmost end of sheath 120 (shown in FIG. 4). Similarly, proximal movement of control device 130a may cause the distalmost end of first tube 160 to be flush with the distalmost end of sheath 120, or extend proximally relative to the distalmost end of sheath 120. Similar movement of control device 130b in the proximal and distal directions may cause similar movement of a second tube 162 (e.g., a working channel), which is attached control device 130b. As with first tube 160, second tube 162 may have a diameter of approximately 2.8 mm, but may be any size and is not limited thereto. It will be understood that second tube 162 may be sized to fit within first lumen 122b, the size of which is also not limited. In some examples, a diameter of second tube 162 may be approximately 1.0 mm to approximately 10.0 mm, and a diameter of first lumen 122b may be approximately 0.010 inches greater than the diameter of second tube 162. In some instances, the diameters of first tube 160 and second tube 162 may be the same, and the diameters of first lumen 122a and first lumen 122b may be the same. It will be understood, however, that these diameters may be different.

Figure 7:
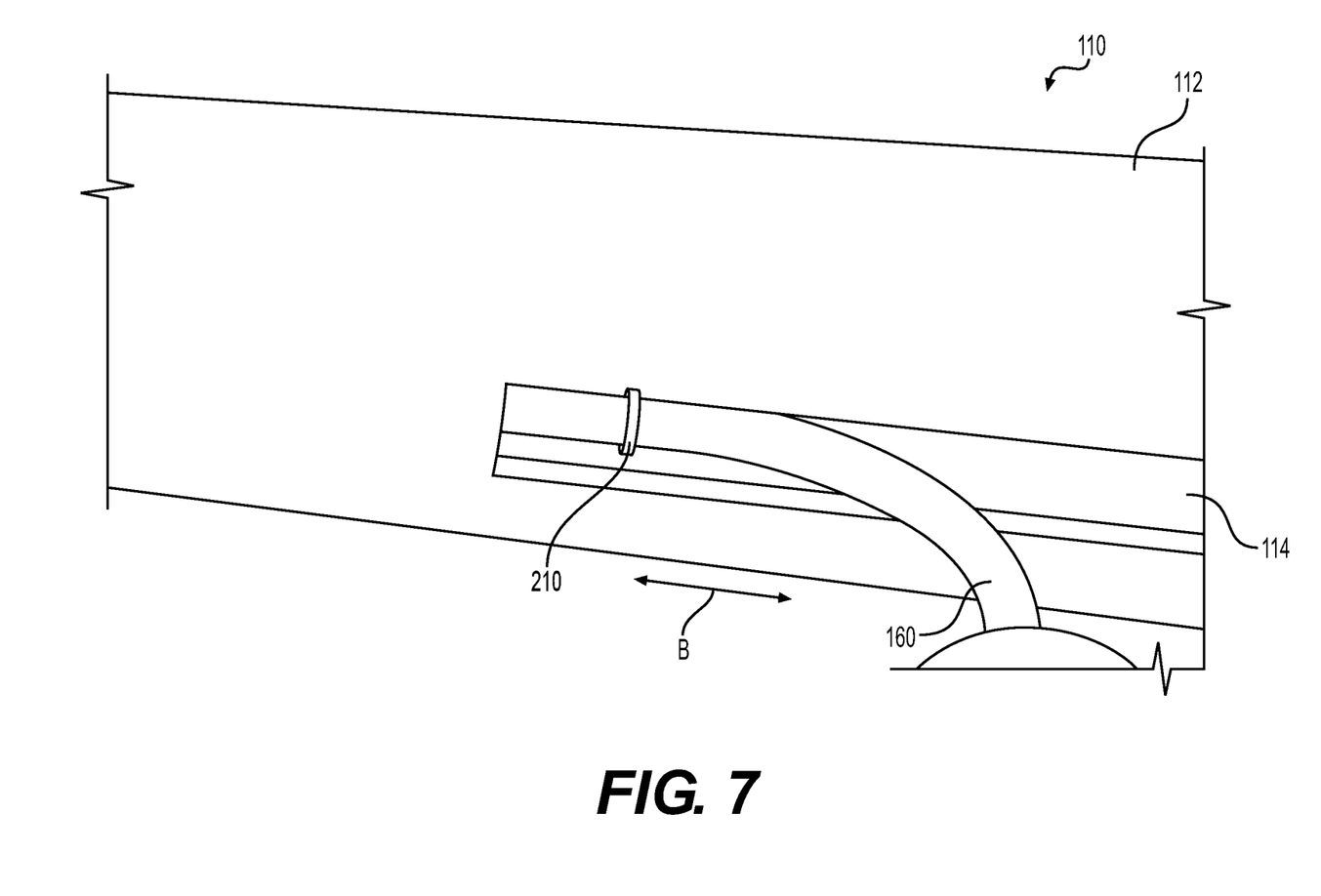
FIG. 7 is a side view of a handle of the endoscope system of FIG. 2, according to an embodiment.

With reference to FIG. 7, a gasket 210, protrusion, or similar device may extend from an outer surface of first tube 160 at the proximal end of first tube 160. While not shown, second tube 162 may also include gasket 210 or other similar device. Gasket 210 may slide within slot 114 and may contact one or more walls of handle 110, which may increase friction between gasket 210 and handle 110. This increased friction may increase the force necessary to move control devices 130a, 130b in the proximal and distal directions. In this situation, gasket 210 may operate similar to a locking mechanism and may help to prevent proximal or distal movement of control devices 130a, 130b relative to handle 110 unless a sufficient force in the proximal or the distal directions is applied to overcome the friction force. In this manner, positions of the distal ends of first tube 160 and/or second tube 162 relative to sheath 120 may be maintained during a medical procedure until a sufficient force is applied to control devices 130a, 130b.

Gasket 210 may additionally or alternatively include additional locking and/or additional friction-increasing members. For example, a ratchet device may be provided to prevent movement of control devices 130a, 130b in the proximal and distal directions unless a sufficient force is provided to overcome the force provided by the ratchet device. Additionally or alternatively, a plurality of protrusions may be provided along the outer surface of handle 110, adjacent each of slots 114. A strap or other device may be attached to control devices 130a, 130b, and may be attached to one or more of the plurality of protrusions and may prevent or reduce movement of control device 130a, 130b in the proximal or the distal directions. In this manner, a position of first and second tubes 160, 162 in the proximal/distal direction may be maintained during a medical procedure.

As mentioned, a cross-section of sheath 120 along lines 6-6 of FIG. 2 is shown in FIG. 6. Sheath 120 includes a first lumen 122a and a second lumen 122b. First tube 160 extends from a proximal end of sheath 120 to a distal end of sheath 120 within first lumen 122a. Second tube 162 similarly extends from the proximal end of sheath 120 to the distal end of sheath 120 within second lumen 122b. Each of first tube 160 and second tube 162 includes a plurality of actuation wires 192, respectively. As described herein, each set of actuation wires 192 comprises any number of wires (four in FIG. 6, but the number is not limited thereto, e.g., two, three, or more). First tube 160 may be extruded around actuation wires 192 such that actuation wires 192 are surrounded by a wall of first tube 160 and connected to first tube 160 along its entire length. Alternatively, actuation wires 192 may be disposed within respective lumen 160a formed within the wall of first tube 160 and actuation wires 192 may be attached only at the distal end of first tube 160. In one or more aspects, actuation wires 192 may be attached at only certain points along first tube 160. Actuation wires 192 may be similarly attached within lumens 162a of second tube 162. In this manner, movement of joysticks 132a, 132b may cause bending (e.g., articulation) of distal ends of first tube 160 and second tube 162, respectively, as described herein.

Figure 4:
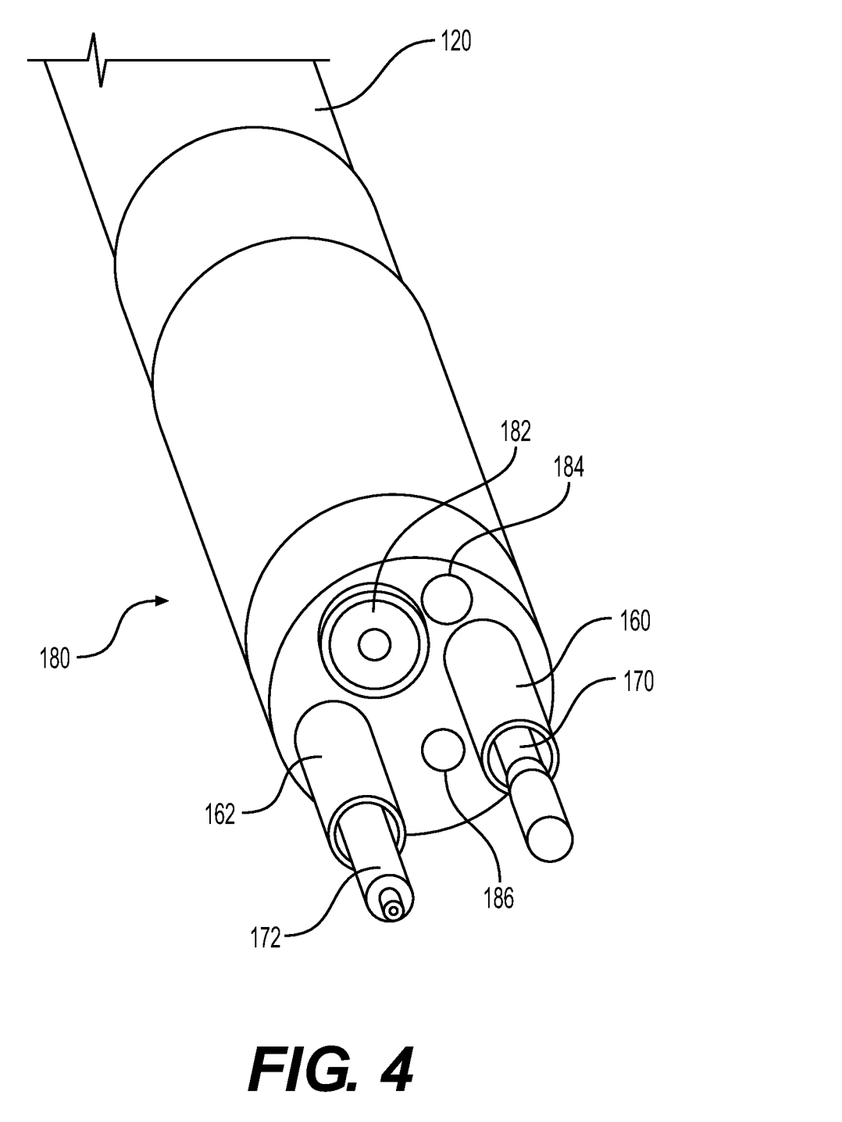
FIG. 4 is a distal end of the endoscope system of FIG. 2, according to an embodiment.

With reference to FIGS. 4 and 6, first tube 160 may extend from handle 110, through first lumen 122a of shaft 120, and may move proximally and distally within first lumen 122a. Second tube 162 may extend from handle 110, through second lumen 122b of shaft 120, and may move proximally and distally within second lumen 122b. Movement of first tube 160 and second tube 162 may be controlled by control device 130a and control device 130b, respectively. For example, movement of control device 130a in a distal direction as shown by arrow B within slot 114 (FIG. 5A) may move first tube 160 in a distal direction within first lumen 122a. Movement of control device 130a in a proximal direction as shown by arrow B within slot 114 may move first tube 160 in a proximal direction within first lumen 122a. Movement of control device 130b in slot 114 may similarly move second tube 162 proximally and distally within second lumen 122b.

Figure 5C:
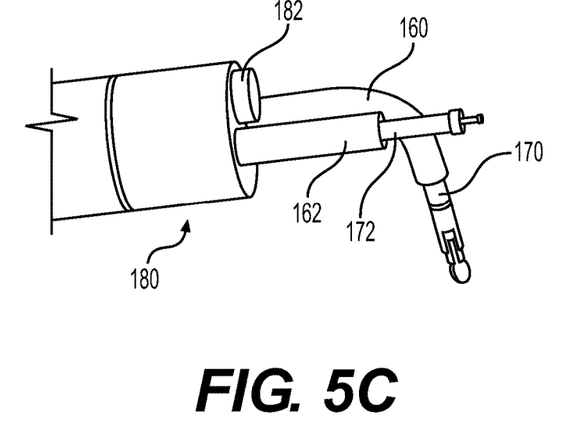
Figure 5D:
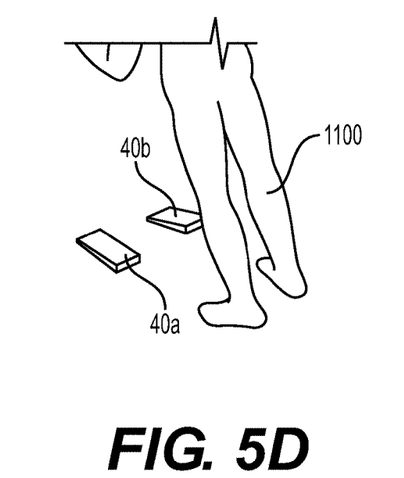
FIG. 5D illustrates actuators of the medical system of FIG. 1, according to an embodiment.
Figure 5E:
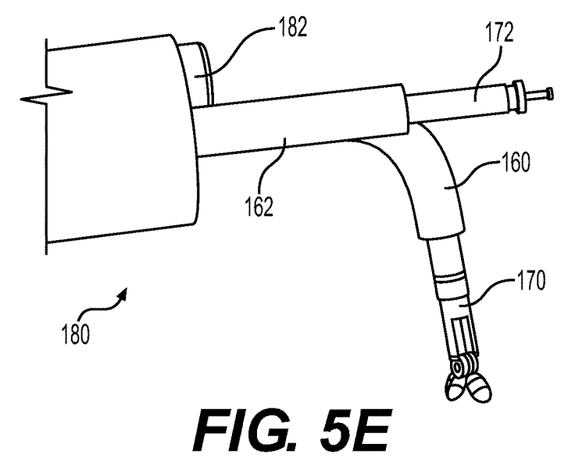
FIGS. 5E and 5F are views of a distal end of the endoscope system of FIG. 2, according to an embodiment.
Figure 5F:
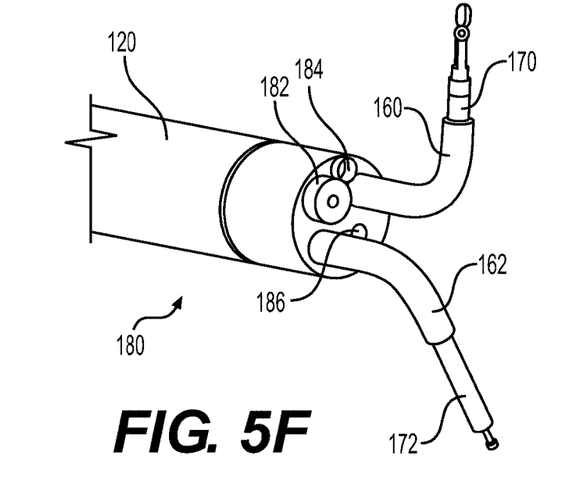

With reference to FIGS. 5C, 5D, and 5E, one or both of first tube 160 and second tube 162 may be bent (e.g., may be articulated) at a predetermined location along a longitudinal axis of first tube 160 or second tube 162 by moving corresponding joystick 132a or joystick 132b. For example, as joystick 132a or joystick 132b is moved in the direction indicated by arrows D in FIG. 5A, actuation wires 192 are pushed or pulled within corresponding wire lumens 160a or 162a, respectively. This movement of wires 192 may cause distal ends of first tube 160 or second tube 162 to bend. For example, first tube 160 or second tube 162 may lie along an axis parallel to longitudinal axis A in a first position (e.g., a neutral position). When the user moves joystick 132a or joystick 132b, the distal ends of corresponding first tube 160 or second tube 162 may bend such that a portion of first tube 160 or a portion of second tube 162 transitions from the first position to a second position, with the second position including a portion of first tube 160 or a portion of second tube 162 extending non-parallel to longitudinal axis A. In other words, first tube 160 and second tube 162 may bend independently of each other in one or more planes, e.g., omnidirectional steerability.

With continued reference to FIG. 6, first tube 160 may include a lumen 166 and second tube 162 may include a lumen 168. Referring to FIGS. 5C, 5D, and 5E, a shaft 170 of first medical instrument 150 (FIG. 2) may extend into and move within lumen 166 of first tube 160, and a shaft 172 of second medical instrument 152 (FIG. 2) may extend into and move within lumen 168 of second tube 162. As shown in FIGS. 5C, 5D, and 5E, distal ends of shafts 170 and 172 may include or be coupled to a medical tool, such as a grasper, a cutting device (scissors, knife, tissue resection device, electrode, etc.), an ablation tool, a forceps (e.g., such as two jaws connected by a hinge), a snare, or any other medical tool. As will be described herein, shafts 170 and 172 may extend from distalmost ends of first tube 160 and second tube 162, respectively, such that the tools at the distal ends of shafts 170, 172 may be exposed at a target site. Operation of these tools, e.g., opening and closing jaws of a grasping device, will be described herein.

With reference to FIG. 2, each first medical instrument 150 includes a handle 150a and second medical instrument 152 includes a handle 152a. While shown as a plunger-style handle in FIG. 2, handles 150a, 152a may be any medical handle for actuating a tool at a distal end of shafts 170, 172, respectively. Each handle 150a, 152a may be mounted in one of actuating devices 30a, 30b, shown in FIG. 1. For example, handle 150a may be mounted in actuation device 30a, and handle 150b may be mounted in actuating device 30b. Each actuating device 30a, 30b may include a fixed member and a movable member. The fixed member may fix a position of a body of handles 150a, 150b, while the movable member may fix the plunger (or movable portion) of handles 150a, 150b. As described herein, actuation of actuating devices 30a, 30b may cause the movable member to move relative to the fixed member. In this manner, the plunger (or movable portion) of handles 150a, 150b may move relative to the body of the handles 150a, 150b, which may cause operation of the tool or end effector at the distal end of handles 150a, 150b.

Actuating device 30a may be actuated via actuator 40a (either via a wired (not shown) or a wireless connection), and actuating device 30b may be actuated via actuator 40b in a similar manner. Although actuators 40a, 40b are shown as foot pedals in FIG. 1, this disclosure is not so limited, as actuators 40a, 40b may be buttons, levers, knobs, etc., for example, positioned on handle 110, a separate user interface or display, robotic actuators, etc. Alternatively or additionally, actuators 40a, 40b may be voice activated, activated via a motion or a specific blinking sequence of the user (e.g., a motion of a user being captured via a camera), or any other manner known in the art.

As an example, the user may depress actuator 40a with a foot, which may cause actuating device 30a and the plunger of handle 150a to move. This may cause jaws of a tool at the distal end of first medical instrument 150 to move from an open position to a close position. Removing the user's foot from actuator 40a may cause the jaws of the tool to open. As another example, the tool may include a laser fiber, whereby depressing actuator 40a may cause the laser energy to fire, and releasing actuator 40a may cause the laser energy to stop firing. In some examples, depressing actuator 40a may cause an electrode to extend into a tissue and/or energize the electrode. Actuator 40b may be operated in a similar manner as actuator 40a and may cause plunger of handle 152a to move to cause the tool at the distal end of second medical instrument 152 to be actuated. It will be understood that the tools may be any medical tool and handles 150a, 152a are not limited to plunger-style handles. For example, handles 150a, 150b may include knobs or other known actuating members or actuating tools or end effectors of first and second medical instruments 150, 152.

A method of operating medical system 10 will now be described. Shaft 120 may be inserted into a body, e.g., a body of patient 1000 in FIG. 1, via a natural orifice, an incision, or any other opening in the body and advanced to a target site. A medical professional may visualize the target site using one or more light emitting elements 184 and/or visualization device 182 at the distal end of shaft 120, for example, with visualization device 182 coupled to a user interface or display via an umbilicus. First medical instrument 150 may be introduced into lumen 166 of first tube 160 at a proximal end thereof via the opening in locking member 139a of port 136a, and medical instrument 152 may be introduced into lumen 168 of second tube 162 at a proximal end thereof via the opening in the locking member of corresponding control device 130b. First medical instrument 150 and second medical instrument 152 may be introduced into lumens 166, 168, respectively, at any time during the medical procedure, e.g., before or after shaft 120 is inserted into the body of patient 1000. Locking member 139a may be locked or unlocked by rotating locking member clockwise or counterclockwise. Locking member 139a may be locked or unlocked at any time during the procedure to allow first medical instrument 150 and second medical instrument 152 to be moved within lumens 166, 168, respectively After positioning the distal end of shaft 120 at the target site, the user may advance one or both of first tube 160 and second tube 162 in the distal direction such that a distal end of first tube 160 and/or a distal end of second tube 162 extend distally of the distalmost end of shaft 120, as shown by arrow C in FIG. 5B. As described herein, this distal movement of first tube 160 and second tube 162 relative to shaft 120 is caused by a user moving control devices 130a, 130b in the distal direction, indicated by arrow B in FIG. 5A. For example, a user may use a thumb and a forefinger to grasp one or both of control devices 130a, 130b and move control devices distally within slot 114. In this manner, the user may move the distal ends of first tube 160 and/or second tube 162 distal of the distalmost end of shaft 120.

Once first tube 160 or second tube 162 extends distally of the distalmost end of shaft 120, the user may use joystick 132*a* or joystick 132*b* to cause articulation of first tube 160 or second tube 162, respectively. For example, a user may grasp joystick 132*a* in FIG. 5A using a thumb and a forefinger (or any other fingers if desired) and may move joystick 132*a* in any direction as indicated by arrows D in FIG. 5A. For example, a first hand of the user may gasp handle 110, while a second hand of the user may manipulate joystick 132*a* or joystick 132*b*. Alternatively, handle 110 may be fixed, e.g., by support device 40, which may allow the user to use the first hand to manipulate joystick 130*a* and the second hand to manipulate joystick 130*b*. Movement of joystick 132*a* in any 360-degree direction may cause corresponding movement of the distal end of first tube 160, as shown in FIGS. 5C, 5E, and 5F. Movement of joystick 132*a* or joystick 132*b* may impart similar movement in the distal ends of first tube 160 or second tube 162. For example, if joystick 132*a* is moved 30 degrees in one direction, the distal end of first tube 160 may be bent 30 degrees in a corresponding direction. It will be understood that the bend angle of the distal ends of first tube 160 and second tube 162 are not limited to a degree of movement of joystick 132*a* or joystick 132*b*. Prior to, during, or after articulation of joystick 132*a*, first medical instrument 150 may be advanced in the distal direction such that a distal end of sheath 170 and a corresponding tool extend distally of the distalmost end of first tube 160. The user may continue to move joystick 132*a* and/or move sheath 170 within and relative to first tube 160 such that the tool at the distal end of sheath 170, e.g., a grasper, is aligned with the target tissue. It will be understood that a user may visualize the target tissue on a monitor showing images transmitted via visualization device 182, for example, on a user interface or display.

Once the tissue is properly positioned relative to the tools, the user may actuate actuator 40*a* by pressing down on actuator 40*a* with the user's foot. In the event the tool is a grasper, actuation of actuator 40*a* may cause a plunger in the handle of first medical instrument 150 to move in a first direction and cause the jaws of the grasper to close around the tissue. The user may lift the user's foot from actuator 40*a*, which may cause the plunger (or other movable element) in the handle of first medical instrument 150 to move in an opposite direction, which may open the jaws of the tool.

It will be understood that similar articulation of the distal end of tube 162 may be performed using joystick 132*b*. In addition, the user may move sheath 172 of second medical instrument 152 within second tube 162 in a similar manner as described herein (e.g. FIG. 5F). The user may depress or release actuator 40*b* to cause actuation of the handle of medical instrument 152. This may cause a tool at the distal end of sheath 172 to operate (e.g., opening or closing a cutting tool, opening or closing another grasping element, deploying a device using the tool, or any similar operation).

Once the user completes work at the target site, the user may remove shaft 120 from the body. In some instances, one or both of first tube 160 and second tube 162 and/or one or both of first medical instrument 150 and second medical instrument 152 may extend distally of the distalmost end of shaft 120. In one instance, first medical instrument 150 may include a grasping element to grasp tissue, and second medical instrument 152 may include a cutting element to cut or dissect the tissue from the body. For example, it may be desired to remove a portion of the tissue from the target site. In this instance, one or more of the tools may grasp the tissue distally of the distalmost end of shaft 120 and this tissue may be removed from the body by removing shaft 120 from the body. It will be understood that the user may also bend or articulate shaft 120 using knobs 42, 43, which in turn would cause first tube 160 and second tube 162, and any tool extending therein, to be bent in the same direction as shaft 120.

While different medical systems have been described, it will be understood that the particular arrangements of elements in these medical systems are not limited. Moreover, a size and a shape of the catheter or shaft of the medical system, or the medical instruments used with the medical system, and/or the method of deploying the system, are not limited. As described in examples herein, tubes within lumens of an endoscope sheath may be extended distally of a distalmost end of the endoscope sheath and may be independently bent or articulated to provide independent articulation for a medical instrument extending within a lumen of the tube improved visualization and/or access to a target site. For example, in certain procedures, accessing the target site from multiple different directions may improve the results of the medical procedure, may decrease the time of the medical procedure, and may improve recovery times of the patient after the medical procedure. In addition, individual first and second tubes 160, 162 may impart high steering force, high lifting force, shorter articulation radius, and high dissection force. Moreover, providing controls, e.g., control devices 130*a*, 130*b*, on handle 110 may allow a single user to operate medical system 10. For example, the user may use one handle to hold handle 110, and may use the other hand (together with one or both feet) to provide independent and/or simultaneous articulation, translation, and/or actuation of medical tools. It will be understood that more than one operator may use medical system 10, e.g., an assistant, to assist in guiding, positioning, and/or operating medical system 10 within the body.

It will be apparent to those skilled in the art that various modifications and variations can be made to the disclosed device without departing from the scope of the disclosure. For example, the maximum bend angle, the location of the bend in a longitudinal direction of the tube, and the number of tubes extending and moving within the endoscope sheath be modified based on a desired medical therapy. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a handle including a first slot;
   a first control device configured to move within the first slot in a proximal direction and a distal direction;
   a sheath extending from the handle and having a longitudinal axis, the sheath defining a first lumen extending from the handle to a distal end of the sheath; and
   a first tube extending within the first lumen, wherein the first tube includes a tube lumen, wherein the first tube is connected to the first control device and is configured to move between a first position, where a distalmost end of the first tube is flush with or proximal of a distalmost end of the sheath, and a second position, where the distalmost end of the first tube is positioned distal of the distalmost end of the sheath,
   a medical instrument configured to be inserted into the tube lumen, wherein a distalmost end of the medical instrument is configured to extend distally of the distalmost end of the sheath; and a rotatable locking mechanism at a proximal end of the tube lumen, wherein the rotatable locking mechanism is configured to fluidly seal the medical instrument in the tube lumen when the rotatable locking mechanism is in a locked position, and wherein the medical instrument is configured to move within the tube lumen when the rotatable locking mechanism is in an unlocked position, wherein the first slot extends parallel to the longitudinal direction of the sheath.

2. The device of claim 1, wherein the first tube is configured to move between the first position and the second position as the first control device moves from a proximal end of the first slot in the distal direction.

3. The device of claim 1, wherein the first control device includes a locking mechanism configured to prevent movement of the first control device and maintain a position of the first control device relative to the handle in the proximal direction and in the distal direction.

4. The device of claim 3, wherein the locking mechanism includes an annular ring extending radially outward from the first tube, wherein the annular ring contacts a portion of the handle and increases a friction force between the handle and the first tube, and wherein the first control device is configured to move within the first slot when a force sufficient to overcome the friction force of the annular ring is applied to the first control device.

5. The device of claim 1, wherein the first control device includes a joystick, and wherein movement of the joystick is configured to bend a distal end of the first tube at an angle relative to the longitudinal axis of the sheath.

6. The device of claim 5, further comprising:
at least three articulation wires extending from the joystick to the distal end of the first tube, wherein a distal end of each of the at least three articulation wires is attached to the first tube.

7. The device of claim 6, wherein the first tube includes an articulation wire lumen corresponding to each of the at least three articulation wires, and wherein each of the at least three articulation wires extend within the corresponding articulation wire lumens.

8. The device of claim 1, wherein the medical instrument includes a tool at its distal end, and wherein the device further comprises:
an actuator configured to actuate the medical instrument.

9. The device of claim 8, wherein the tool includes a plurality of jaws connected by a hinge, wherein the actuator includes a foot pedal, wherein the plurality of jaws are configured to move from an open position to a closed position when the foot pedal is depressed, and wherein the plurality of jaws is configured to move from the closed position to the open position when the foot pedal is released.

10. The device of claim 1, further comprising:
a second lumen within the sheath and extending from the handle to the distal end of the sheath; and
a second tube extending within the second lumen, wherein the second tube is configured to move between a first position, where a distalmost end of the second tube is flush with or proximal of the distalmost end of the sheath, and a second position, where the distalmost end of the second tube is positioned distal of the distalmost end of the sheath.

11. The device of claim 10, further comprising:
a second slot; and
a second control device configured to move within the second slot, wherein the second control device includes a second joystick configured to cause a distal end of the second tube to bend.

12. The device of claim 11, wherein the first control device and the second control device are configured to move independently of each other, and wherein the first tube and the second tube are configured to bend independently of each other.

13. The device of claim 1, wherein the handle includes a first handle actuator and a second handle actuator configured to deflect a portion of the sheath.

* * * * *